(12) United States Patent
Viola

(10) Patent No.: US 7,617,961 B2
(45) Date of Patent: Nov. 17, 2009

(54) TOOL ASSEMBLY FOR SURGICAL STAPLING DEVICE

(75) Inventor: Frank J. Viola, Sandy Hook, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 658 days.

(21) Appl. No.: 10/529,568

(22) PCT Filed: Oct. 6, 2003

(86) PCT No.: PCT/US03/31653

§ 371 (c)(1),
(2), (4) Date: Mar. 28, 2005

(87) PCT Pub. No.: WO2004/032754

PCT Pub. Date: Apr. 22, 2004

(65) Prior Publication Data

US 2006/0100644 A1    May 11, 2006

Related U.S. Application Data

(60) Provisional application No. 60/416,056, filed on Oct. 4, 2002.

(51) Int. Cl.
*A61B 17/068* (2006.01)
(52) U.S. Cl. ............ 227/175.1; 227/19; 227/175.2; 227/175.3; 227/176.1
(58) Field of Classification Search .......... 227/19, 227/175.1, 175.2, 175.3, 176.1
See application file for complete search history.

(56) References Cited

U.S. PATENT DOCUMENTS

| | | | |
|---|---|---|---|
| 3,079,606 A | 3/1963 | Bobrov et al. | |
| 3,490,675 A | 1/1970 | Green et al. | |
| 4,429,695 A | 2/1984 | Green | |
| 4,505,414 A | 3/1985 | Filipi | |
| 4,589,413 A | 5/1986 | Malyshev et al. | |
| 4,602,634 A | 7/1986 | Barkley | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,671,445 A | 6/1987 | Barker et al. | |

(Continued)

FOREIGN PATENT DOCUMENTS

DE    2744824    4/1978

(Continued)

*Primary Examiner*—Rinaldi I. Rada
*Assistant Examiner*—Michelle Lopez

(57) ABSTRACT

The present invention includes a tool assembly with a first jaw movable in relation to a second jaw between a spaced position and an approximated position. An approximation member is movable in relation to the first jaw to effect movement of the first and second jaws from the spaced position to the approximated position. A cam channel is configured to approximate the distal ends of the first and second jaws prior to approximation of the proximal ends of the first and second jaws. An articulation and firing actuator includes a flexible band having first and second end portions, wherein movement of either the first or the second end portion of the band effects pivoting of the tool assembly, and movement of the both end portions of the band, simultaneously, effects movement of a dynamic clamping member to eject staples from a cartridge assembly.

15 Claims, 5 Drawing Sheets

U.S. PATENT DOCUMENTS

| | | |
|---|---|---|
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,892,244 A | 1/1990 | Fox et al. |
| 4,978,049 A | 12/1990 | Green |
| 4,991,764 A | 2/1991 | Mericle |
| 5,040,715 A | 8/1991 | Green et al. |
| 5,065,929 A | 11/1991 | Schulze et al. |
| 5,074,454 A | 12/1991 | Peters |
| 5,083,695 A | 1/1992 | Foslien et al. |
| 5,084,057 A | 1/1992 | Green et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,170,925 A | 12/1992 | Madden et al. |
| 5,246,156 A | 9/1993 | Rothfuss et al. |
| RE34,519 E | 1/1994 | Fox et al. |
| 5,282,807 A | 2/1994 | Knoepfler |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lori |
| 5,332,142 A | 7/1994 | Robinson et al. |
| 5,336,232 A | 8/1994 | Green et al. |
| 5,358,506 A | 10/1994 | Green et al. |
| 5,364,002 A | 11/1994 | Green et al. |
| 5,364,003 A | 11/1994 | Williamson, IV |
| 5,376,095 A | 12/1994 | Ortiz |
| 5,381,943 A | 1/1995 | Allen et al. |
| 5,382,255 A | 1/1995 | Castro et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Minck, Jr. et al. |
| 5,535,937 A | 7/1996 | Boiarski et al. |
| 5,540,375 A | 7/1996 | Bolanos et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,573,543 A | 11/1996 | Akopov et al. |
| 5,575,799 A | 11/1996 | Bolanos et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,542 A | 12/1997 | Knodel et al. |
| 5,704,534 A | 1/1998 | Huitema et al. |
| 5,709,334 A | 1/1998 | Sorrentino et al. |
| 5,711,472 A | 1/1998 | Bryan |
| 5,713,505 A | 2/1998 | Huitema |
| 5,716,366 A | 2/1998 | Yates |
| 5,725,536 A | 3/1998 | Oberlin et al. |
| 5,725,554 A | 3/1998 | Simon et al. |
| 5,728,110 A | 3/1998 | Vidal et al. |
| 5,735,848 A | 4/1998 | Yates et al. |
| 5,743,456 A | 4/1998 | Jones et al. |
| 5,749,893 A | 5/1998 | Redmond et al. |

| | | | | | | |
|---|---|---|---|---|---|---|
| 5,752,644 | A | 5/1998 | Bolanos et al. | 6,698,643 B2 | 3/2004 | Whitman |
| 5,762,255 | A | 6/1998 | Chrisman et al. | 6,716,232 B1 | 4/2004 | Vidal et al. |
| 5,762,256 | A | 6/1998 | Mastri et al. | 6,722,552 B2 | 4/2004 | Fenton, Jr. |
| 5,769,303 | A | 6/1998 | Knodel et al. | 6,731,473 B2 | 5/2004 | Li et al. |
| 5,772,673 | A | 6/1998 | Cuny et al. | 6,755,338 B2 | 6/2004 | Hahnen et al. |
| 5,779,130 | A | 7/1998 | Alesi et al. | 6,783,524 B2 | 8/2004 | Anderson et al. |
| 5,779,131 | A | 7/1998 | Knodel et al. | 6,786,382 B1 | 9/2004 | Hoffman |
| 5,779,132 | A | 7/1998 | Knodel et al. | 6,808,262 B2 | 10/2004 | Chapoy et al. |
| 5,782,396 | A | 7/1998 | Mastri et al. | 6,830,174 B2 | 12/2004 | Hillstead et al. |
| 5,782,397 | A | 7/1998 | Koukline | 6,835,119 B2 | 12/2004 | Hori |
| 5,782,834 | A | 7/1998 | Lucey et al. | 6,843,403 B2 | 1/2005 | Whitman |
| 5,797,536 | A | 8/1998 | Smith et al. | RE38,708 E | 3/2005 | Bolanos et al. |
| 5,797,537 | A | 8/1998 | Oberlin et al. | 6,877,647 B2 | 4/2005 | Green et al. |
| 5,797,538 | A | 8/1998 | Heaton et al. | 6,879,880 B2 | 4/2005 | Nowlin et al. |
| 5,810,811 | A | 9/1998 | Yates et al. | 6,889,116 B2 | 5/2005 | Jinno |
| 5,810,855 | A | 9/1998 | Rayburn et al. | 6,905,057 B2 | 6/2005 | Swayze et al. |
| 5,814,055 | A | 9/1998 | Knodel et al. | 2001/0030219 A1 | 10/2001 | Palmer et al. |
| 5,816,471 | A | 10/1998 | Plyley et al. | 2002/0004498 A1 | 1/2002 | Doherty |
| 5,817,109 | A | 10/1998 | McGarry et al. | 2002/0009193 A1 | 1/2002 | Deguchi |
| 5,820,009 | A | 10/1998 | Melling et al. | 2002/0018323 A1 | 2/2002 | Li |
| 5,823,066 | A | 10/1998 | Huitema et al. | 2002/0032948 A1 | 3/2002 | Ahn |
| 5,826,776 | A | 10/1998 | Schulze et al. | 2002/0036748 A1 | 3/2002 | Chapoy |
| 5,829,662 | A | 11/1998 | Allen et al. | 2002/0045442 A1 | 4/2002 | Silen et al. |
| 5,833,695 | A | 11/1998 | Yoon | 2002/0069565 A1 | 6/2002 | Liao |
| 5,836,147 | A | 11/1998 | Schnipke | 2002/0084304 A1 | 7/2002 | Whitman |
| 5,862,972 | A | 1/1999 | Green et al. | 2002/0111621 A1 | 8/2002 | Wallace |
| 5,865,361 | A | 2/1999 | Milliman et al. | 2002/0143346 A1 | 10/2002 | McGuckin |
| 5,871,135 | A | 2/1999 | Williamson, IV et al. | 2002/0177843 A1 | 11/2002 | Anderson |
| 5,873,873 | A | 2/1999 | Smith et al. | 2002/0188294 A1 | 12/2002 | Couture |
| 5,897,562 | A | 4/1999 | Bolanos et al. | 2002/0190093 A1 | 12/2002 | Fenton |
| 5,901,895 | A | 5/1999 | Heaton et al. | 2003/0009193 A1 | 1/2003 | Corsaro |
| 5,911,353 | A | 6/1999 | Bolanos et al. | 2003/0105476 A1 | 6/2003 | Sancoff |
| 5,918,791 | A | 7/1999 | Sorrentino et al. | 2003/0132268 A1 | 7/2003 | Whitman |
| 5,919,198 | A | 7/1999 | Graves, Jr. et al. | 2004/0004105 A1 | 1/2004 | Jankowski |
| 5,922,001 | A | 7/1999 | Yoon | 2004/0007608 A1 | 1/2004 | Ehrenfels |
| 5,954,259 | A | 9/1999 | Viola et al. | 2004/0050902 A1 | 3/2004 | Green et al. |
| 5,980,510 | A | 11/1999 | Tsonton et al. | 2004/0093029 A1 | 5/2004 | Zubik |
| 6,004,335 | A | 12/1999 | Vaitekunas et al. | 2004/0094597 A1 | 5/2004 | Whitman |
| 6,010,054 | A | 1/2000 | Johnson et al. | 2004/0108357 A1 | 6/2004 | Milliman |
| 6,032,849 | A | 3/2000 | Mastri et al. | 2004/0149802 A1 | 8/2004 | Whitman |
| 6,079,606 | A | 6/2000 | Milliman et al. | 2004/0173659 A1 | 9/2004 | Green |
| 6,109,500 | A | 8/2000 | Alli et al. | 2004/0199181 A1 | 10/2004 | Knodel |
| 6,197,017 | B1 | 3/2001 | Brock et al. | 2004/0232199 A1 | 11/2004 | Shelton |
| 6,202,914 | B1 | 3/2001 | Geiste et al. | 2004/0232200 A1 | 11/2004 | Shelton |
| 6,241,139 | B1 | 6/2001 | Milliman et al. | 2004/0232201 A1 | 11/2004 | Wenchell |
| 6,250,532 | B1 | 6/2001 | Green et al. | 2004/0243151 A1 | 12/2004 | Demmy |
| 6,264,086 | B1 | 7/2001 | McGuckin, Jr. | 2004/0267310 A1 | 12/2004 | Racenet |
| 6,264,087 | B1 | 7/2001 | Whitman | 2005/0006429 A1 | 1/2005 | Wales |
| 6,269,977 | B1 | 8/2001 | Moore | 2005/0006430 A1 | 1/2005 | Wales |
| 6,279,809 | B1 | 8/2001 | Nicolo | 2005/0006431 A1 | 1/2005 | Shelton |
| 6,315,183 | B1 | 11/2001 | Piraka | 2005/0006432 A1 | 1/2005 | Racenet |
| 6,315,184 | B1 | 11/2001 | Whitman | 2005/0006433 A1 | 1/2005 | Milliman |
| 6,325,810 | B1 | 12/2001 | Hamilton et al. | 2005/0006434 A1 | 1/2005 | Wales |
| 6,330,965 | B1 | 12/2001 | Milliman et al. | 2005/0023324 A1 | 2/2005 | Doll |
| 6,436,097 | B1 | 8/2002 | Nardella | 2005/0023325 A1 | 2/2005 | Gresham |
| 6,439,446 | B1 | 8/2002 | Perry et al. | 2005/0067457 A1 | 3/2005 | Shelton |
| 6,443,973 | B1 | 9/2002 | Whitman | 2005/0067458 A1 | 3/2005 | Swayze |
| 6,463,623 | B2 | 10/2002 | Ahn et al. | 2005/0067459 A1 | 3/2005 | Swayze et al. |
| 6,488,196 | B1 | 12/2002 | Fenton, Jr. | 2005/0067460 A1 | 3/2005 | Milliman |
| 6,503,257 | B2 | 1/2003 | Grant et al. | 2005/0072827 A1 | 4/2005 | Mollenauer |
| 6,505,768 | B2 | 1/2003 | Whitman | 2005/0103819 A1 | 5/2005 | Racenet |
| 6,544,274 | B2 | 4/2003 | Danitz et al. | 2005/0119669 A1 | 6/2005 | Demmy |
| 6,554,844 | B2 | 4/2003 | Lee et al. | 2005/0127131 A1 | 6/2005 | Mastri |
| 6,565,554 | B1 | 5/2003 | Niemeyer | | | |
| 6,587,750 | B2 | 7/2003 | Gerbi et al. | | | |
| 6,592,597 | B2 | 7/2003 | Grant et al. | | | |
| 6,594,552 | B1 | 7/2003 | Nowlin et al. | DE | 2903159 | 1/1980 |
| 6,602,252 | B2 | 8/2003 | Mollenauer | DE | 4213426 | 10/1992 |
| 6,612,053 | B2 | 9/2003 | Liao | DE | 4300307 | 7/1994 |
| 6,619,529 | B2 | 9/2003 | Green et al. | EP | 0041022 | 12/1981 |
| 6,644,532 | B2 | 11/2003 | Green et al. | EP | 0136950 | 4/1985 |
| 6,656,193 | B2 | 12/2003 | Grant et al. | EP | 0140552 | 5/1985 |
| 6,669,073 | B2 | 12/2003 | Milliman et al. | EP | 0156774 | 10/1985 |

FOREIGN PATENT DOCUMENTS

| | | | | | |
|---|---|---|---|---|---|
| EP | 0216532 | 4/1987 | EP | 0598202 | 5/1994 |
| EP | 0220029 | 4/1987 | EP | 0598579 | 5/1994 |
| EP | 0213817 | 11/1987 | EP | 0621006 | 10/1994 |
| EP | 0273468 | 7/1988 | EP | 0621009 | 10/1994 |
| EP | 0324166 | 7/1989 | EP | 0656188 | 6/1995 |
| EP | 0324635 | 7/1989 | EP | 0365153 | 8/1995 |
| EP | 0324637 | 7/1989 | EP | 0666057 | 8/1995 |
| EP | 0324638 | 7/1989 | EP | 0705571 | 4/1996 |
| EP | 0369324 | 5/1990 | EP | 0800792 A | 10/1997 |
| EP | 0373762 | 6/1990 | FR | 2542188 | 9/1984 |
| EP | 0380025 | 8/1990 | FR | 2681775 | 10/1991 |
| EP | 0399701 | 11/1990 | GB | 1352554 | 4/1971 |
| EP | 0449394 | 10/1991 | GB | 1452185 | 10/1976 |
| EP | 0484677 | 5/1992 | GB | 1555455 | 11/1979 |
| EP | 0489436 | 6/1992 | GB | 2048685 | 12/1980 |
| EP | 0503662 | 9/1992 | GB | 2070499 | 9/1981 |
| EP | 0514139 | 11/1992 | GB | 2141066 | 12/1984 |
| EP | 0536903 | 4/1993 | GB | 2165559 | 4/1986 |
| EP | 0537572 | 4/1993 | SU | 728848 | 5/1977 |
| EP | 0539762 | 5/1993 | SU | 659146 | 4/1979 |
| EP | 0545029 | 6/1993 | SU | 980703 | 12/1982 |
| EP | 0552050 | 7/1993 | SU | 990220 | 1/1983 |
| EP | 0552423 | 7/1993 | WO | WO 89/10094 | 11/1989 |
| EP | 0579038 | 1/1994 | WO | WO9210976 | 7/1992 |
| EP | 0589306 | 3/1994 | WO | 9308754 | 5/1993 |
| EP | 0591946 | 4/1994 | WO | WO8302247 | 7/1993 |
| EP | 0592243 | 4/1994 | WO | 9314706 | 8/1993 |
| EP | 0593920 | 4/1994 | | | |

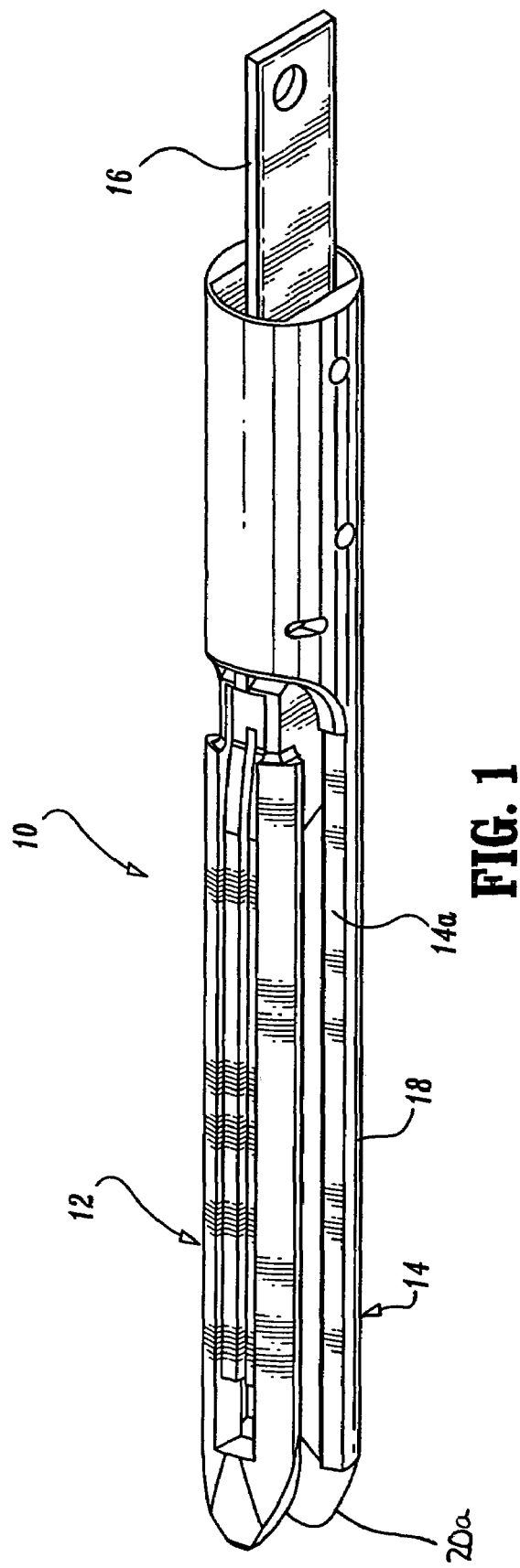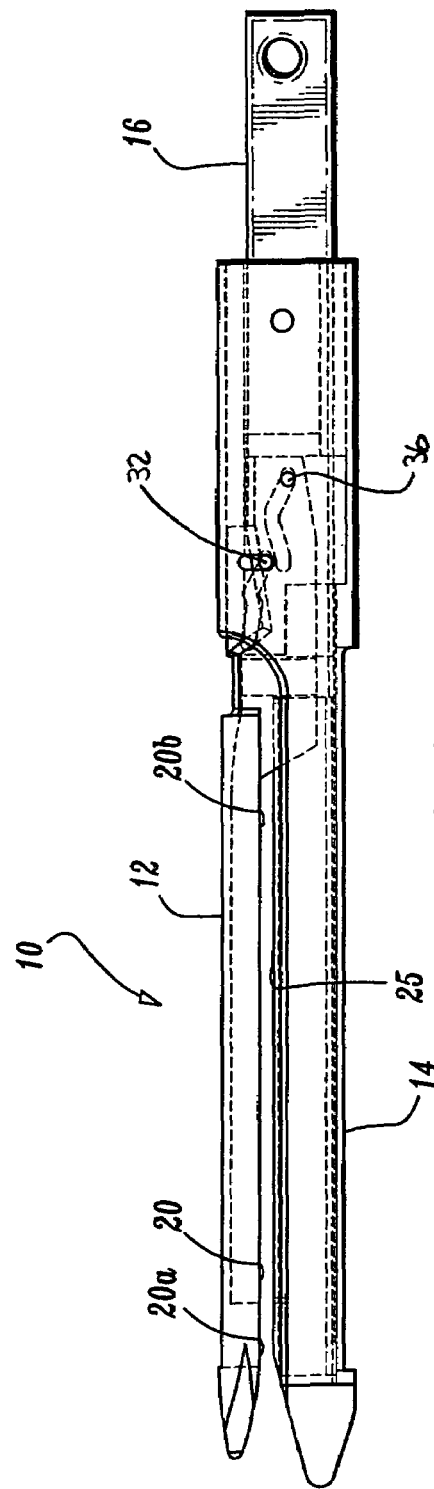

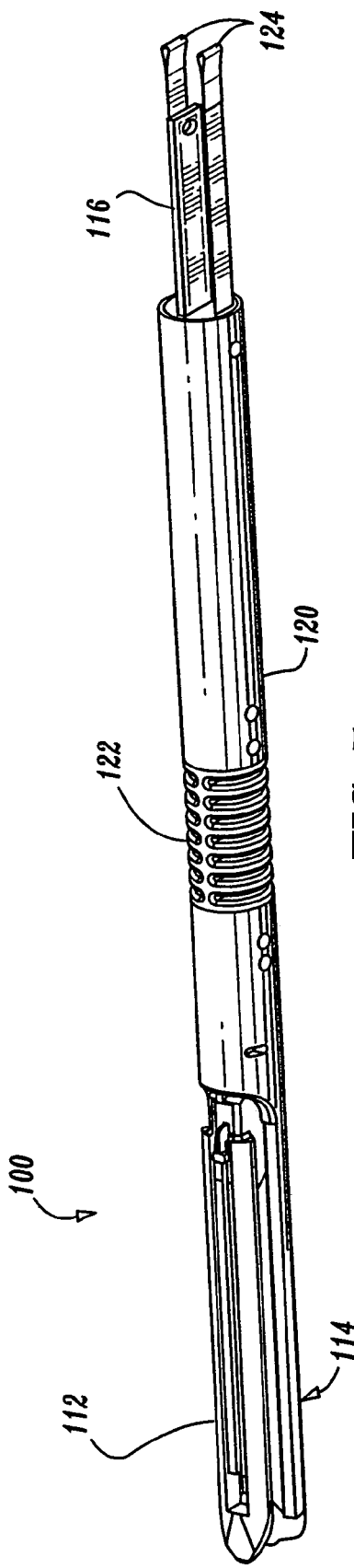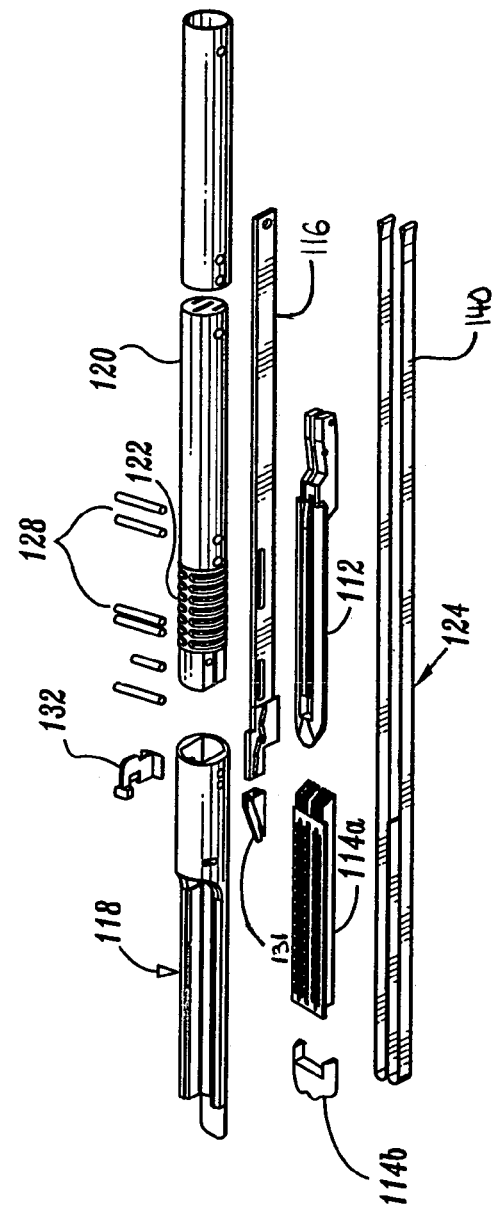
FIG. 5
FIG. 6

TOOL ASSEMBLY FOR SURGICAL STAPLING DEVICE

CROSS REFERENCE TO RELATED APPLICATIONS

This is a National Stage Application of PCT/US03/31653 under 35 USC §371(a), which claims priority of U.S. Provisional Patent Application Ser. No. 60/416,056 filed Oct. 4, 2002, entitled "Tool Assembly for Surgical Stapling Device", now abandoned, the disclosures of which are hereby incorporated by reference in their entirety.

BACKGROUND

1. Technical Field

The present disclosure relates generally to a surgical tool assembly for manipulating and/or applying fasteners to tissue. More specifically, the present disclosure relates to a surgical tool assembly having a pair of jaws including a unique approximation mechanism to facilitate improved clamping and manipulation of tissue.

2. Background of Related Art

Surgical staplers and tool assemblies for clamping tissue between opposed jaw structure of a tool assembly and thereafter fastening the clamped tissue are well known in the art. These devices may include a knife for incising the fastened tissue. Such staplers having laparoscopic or endoscopic configurations are also well known in the art. Examples of endoscopic surgical staplers of this type are described in U.S. Pat. Nos. 6,330,965, 6,250,532, 6,241,139, 6,109,500 and 6,079,606, all of which are incorporated herein by reference in their entirety.

Typically, such staplers include a tool member or assembly having a pair of jaws including a staple cartridge for housing a plurality of staples arranged in at least two laterally spaced rows and an anvil which includes a plurality of staple forming pockets for receiving and forming staple legs of the staples as the staples are driven from the cartridge. The anvil and cartridge are pivotally supported adjacent each other and are pivotable in relation to each other between open and closed positions. In use, tissue is positioned between the jaws in the open position and the jaws are pivoted to the closed position to clamp tissue therebetween.

One problem associated with conventional staplers and tool assemblies is that as the anvil and cartridge pivot in relation to each other, closure occurs first at the proximal end of the jaws and thereafter at the distal end of the jaws. This sequence of jaw closure has the effect of moving tissue positioned between the jaws towards the distal end of the jaws, thus, forcing tissue from the jaws.

During laparoscopic or endoscopic procedures, access to a surgical site is achieved through a small incision or through a narrow cannula inserted through a small entrance wound in a patient. Because of the limited area available to access the surgical site, endoscopic staplers are sometimes used to grasp and/or manipulate tissue. Conventional staplers having an anvil or cartridge mounted to a fixed pivot point which are pivotable to a closed position are not particularly suited for grasping tissue because only a limited clamping force is produced at the distal end of the jaws.

Accordingly, a need exists for an endoscopic surgical stapling tool member or assembly having pivotal jaws which can be operated to effectively grasp, manipulate and/or fasten tissue, including with the end of the jaws, without, or while minimizing, distal movement of the tissue positioned between the jaws.

SUMMARY

In accordance with the present disclosure, a tool assembly having a pair of jaws is disclosed. Each of the jaws has a proximal end and a distal end and the first jaw is movable in relation to the second jaw between a spaced position and an approximated position. First and second cam followers are supported on the first jaw. An approximation member is movable in relation to the first jaw and includes at least one cam surface positioned to engage the first and second cam followers. The approximation member is movable in relation to the first jaw to move the at least one cam surface in relation to the first and second cam followers to effect movement of the first and second jaws from the spaced position to the approximated position. The at least one cam channel is configured to approximate the distal ends of the first and second jaws prior to approximation of the proximal ends of the first and second jaws. By approximating the distal ends of the first and second jaws first, tissue positioned between the jaws is not pushed forward within the jaws during closure of the jaws. Further, the jaws are better able to grip and manipulate tissue using the distal ends of the jaws.

Preferably, the first jaw includes an anvil and the second jaw includes a cartridge assembly housing a plurality of staples. In a preferred embodiment, the at least one cam surface includes first and second cam channels, and the approximation member includes a flat plate having the cam channels formed therein. The first jaw includes a longitudinal slot formed in its proximal end and the approximation member is being slidably positioned in the longitudinal slot. The first and second cam followers are supported on the proximal end of the first jaw and extend across the longitudinal slot adjacent the first and second cam channels. The first cam follower extends through the first cam channel and the second cam follower extends through the second cam channel. Preferably, the tool assembly is pivotally attached to a body portion by an articulation joint. The body portion may form the distal end of a surgical stapling device or a proximal portion of a disposable loading unit.

In another preferred embodiment, the tool assembly includes an anvil, a cartridge assembly housing a plurality of staples and a dynamic clamping member. The anvil and cartridge assembly are movable in relation to each other between spaced and approximated positions. The dynamic clamping member is movable in relation to the anvil and the cartridge assembly to eject the staples from the cartridge assembly. The tool assembly is pivotally attached to a body portion and is pivotable in relation to the body portion from a position aligned with the longitudinal axis of the body portion to a position oriented at an angle to the longitudinal axis of the body portion. An articulation and firing actuator extends at least partially through the body portion and the tool assembly. The articulation and firing actuator is operably associated with the dynamic clamping member and the tool assembly and is movable in relation thereto to selectively pivot the tool assembly in relation to the body portion and/or move the dynamic clamping member in relation to the tool assembly to eject the staples from the cartridge.

Preferably, the articulation and firing actuator includes a flexible band having a first end portion extending at least partially through the body portion and through the cartridge assembly, a central portion extending from the first end portion operably associated with the dynamic clamping member and a second end portion extending from the central portion through the cartridge assembly and at least partially through the body portion to a position adjacent the first end. The articulation and firing actuator is operably associated with the tool assembly such movement of either the first end portion or the second end portion of the flexible band proximally and independently of the other end portion effects pivoting of the tool assembly in relation to the body portion, and movement of both the first and second end portions of the flexible band simultaneously effects movement of the dynamic clamping member to eject the staples from the cartridge assembly. In a preferred embodiment, an approximation member is operably associated with the tool assembly and is movable in relation to the tool assembly to move the anvil and cartridge assembly from the spaced to the approximated position.

BRIEF DESCRIPTION OF THE DRAWINGS

Various preferred embodiments of the presently disclosed tool assembly for use with a surgical stapling device are disclosed herein with reference to the drawings, wherein:

FIG. 1 is a side perspective view of one preferred embodiment of the presently disclosed tool assembly in the approximated position;

FIG. 2 is a side view of the tool assembly shown in FIG. 1;

FIG. 5 is a side perspective view of another preferred embodiment of the presently disclosed tool assembly in the approximated position;

FIG. 6 is a side, exploded perspective view of the tool assembly shown in FIG. 5;

DETAILED DESCRIPTION OF PREFERRED EMBODIMENTS

Figure 3:
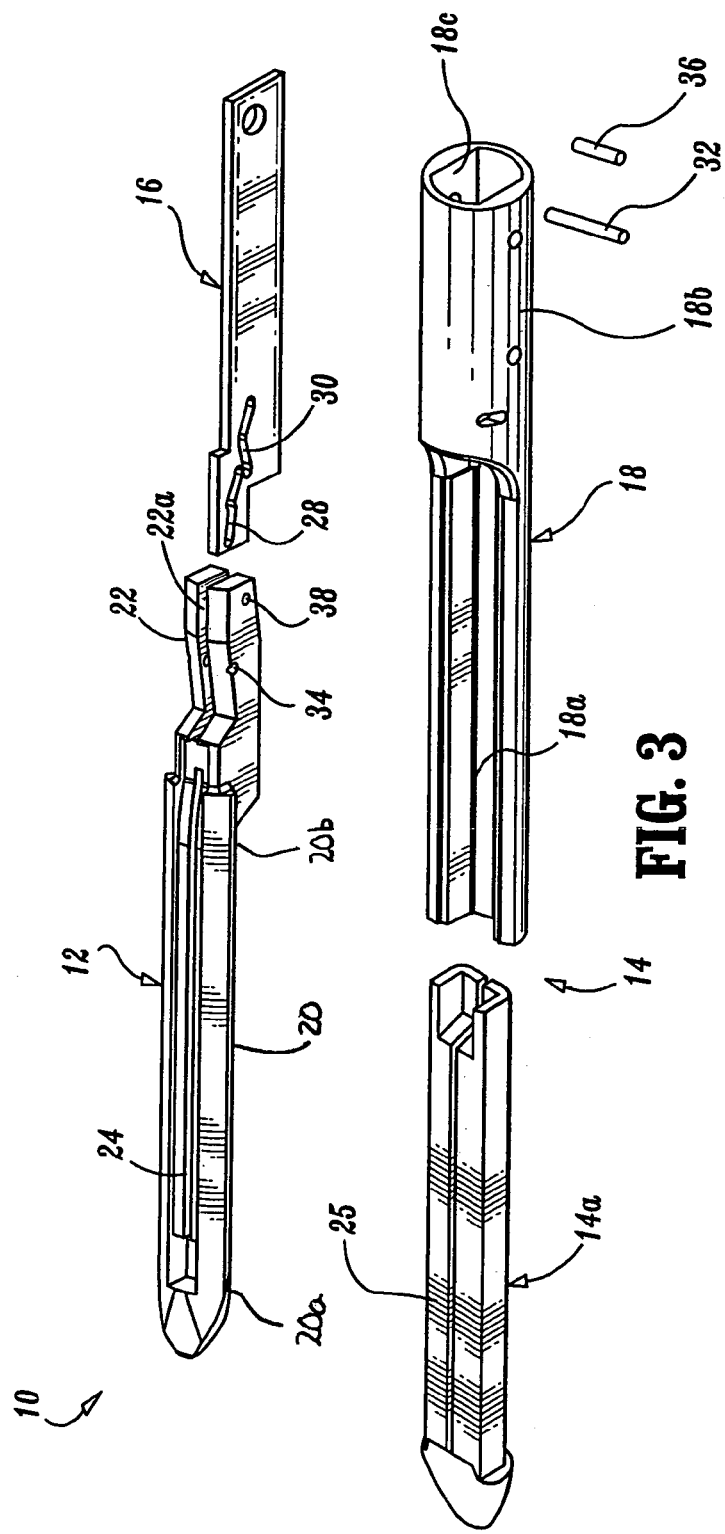
FIG. 3 is a side, exploded perspective view of the tool assembly shown in FIG. 1.

Preferred embodiments of the presently disclosed tool assembly for a stapling device will now be described in detail with reference to the drawings in which like reference numerals designate identical or corresponding elements in each of the several views.

FIGS. 1-3 illustrate one preferred embodiment of the presently disclosed tool assembly shown generally as 10 for use with a surgical stapling device. Tool assembly 10 includes a pair of jaws including an anvil 12 and a cartridge assembly 14 and an approximation member 16. Cartridge assembly 14 includes a support channel 18 for receiving a staple cartridge 14a. Support channel 18 includes distal open channel portion 18a and a proximal portion 18b defining a truncated cylinder 18c. Although not shown in detail, staple cartridge 14a houses a plurality of staples and can include conventional pushers (not shown) for translating movement of a staple drive assembly that typically includes a sled (e.g., 131 in FIG. 6) to movement of the staples through openings or slots in a tissue engaging surface 25 of cartridge 14a.

Anvil 12 has a tissue engaging surface 20 having a distal end 20a and a proximal end 20b and a proximal body portion 22. A longitudinal slot 24 extends along the central longitudinal axis of anvil 12 through tissue engaging surface 20 and is dimensioned to slidably receive a portion of a drive assembly. The drive assembly typically includes a drive bar, a closure assembly, a sled, and a plurality of pushers. The drive assembly functions to eject staples from the cartridge and preferably also maintains a desired uniform tissue gap between the cartridge and the anvil during firing of the device. Proximal body portion 22 of anvil 12 is dimensioned to be generally pivotably received within truncated cylinder 18c of proximal portion 18b of support channel 18 such that tissue engaging surface 20 of anvil 12 is pivotable from a position spaced from tissue engaging surface 25 of cartridge 14a to an approximated position in juxtaposed alignment therewith.

Tool assembly 10 includes an approximation member 16 having one or more cam channels 28 and 30. Preferably, approximation member includes a pair of cam channels although a single cam channel having a pair of cam surfaces is envisioned. Approximation member 16 is dimensioned to be linearly slidable through proximal portion 18b of channel 18 and through a slot 22a formed in proximal body portion 22 of anvil 12. A cam follower 32 extends through a bore 34 formed in proximal portion 22 of anvil 12 and through a hole 35 in proximal portion 18b of support channel 18 and is positioned within cam channel 28. A cam follower 36 extends through a second bore 38 formed in the proximal portion 22 of anvil 12 and through a hole 39 in proximal portion and is positioned within cam channel 30. When approximation member 16 is advanced through slot 22a in proximal portion 22 of anvil 12, cam followers 32 and 36 move through cam channels 28 and 30, respectively. Since approximation member 16 is confined to linear movement within slot 22a, movement of approximation member 16 in a distal direction effects pivotal movement of anvil 12 from the open or spaced position to the closed or approximated position. The angles of the cam slots can be configured to provide a great variety of approximation motions to improve mechanical advantage and achieve specific results, e.g., grasping of tissue.

Figure 4C:
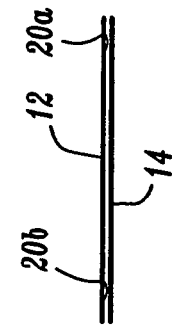
FIG. 4C is a schematic view of the jaws shown in FIG. 4B in an approximated position.
Figure 4B:
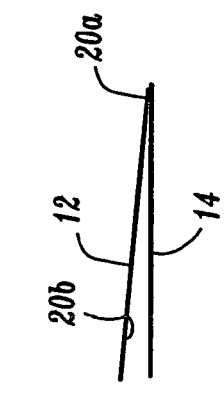
FIG. 4B is a schematic view of the jaws shown in FIG. 4A at a second stage of jaw approximation.
Figure 4A:
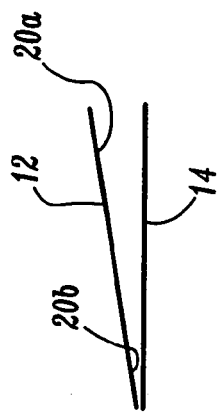
FIG. 4A is a schematic view of the jaws of the tool assembly shown in FIG. 1 at a first stage of jaw approximation.

Referring also to FIGS. 4A-4C, cam channels 28 and 30 preferably are configured to pivot anvil 12 from an open position (FIG. 4A) towards cartridge assembly 14 in a controlled manner to initially facilitate grasping of tissue and thereafter provide for substantially parallel closure of the anvil and cartridge assembly. More specifically, cam channels 28 and 30 are preferably configured to position the distal end 20a of tissue contact surface 20 of anvil 12 substantially in contact with cartridge 14 (FIG. 4B) during the initial portion of an actuating stroke of approximation member 16. This facilitates grasping of tissue even very thin tissue. During a second portion of the actuating stroke of approximation member 16, distal end 20a of anvil 12 is moved away from cartridge assembly 14 to a resultant position in which tissue engaging surface 20 of anvil 12 is parallel or substantially parallel to tissue engaging surface 25 of cartridge assembly 14. During the final portion of the actuating stroke of approximation member 16, the anvil 12 and cartridge assembly 14 are brought together in parallel or substantially parallel closure to define a desired tissue gap (FIG. 4C). It is noted that any desired motion of anvil 12 can be achieved using the cam followers described herein. By moving anvil 12 in relation to cartridge assembly 14 from the spaced to the approximated position in the manner described above i.e., front or distal to back or proximal closure, the tendency for tissue to move forward within the jaws, as in conventional devices, is substantially eliminated.

Although approximation member 16 is illustrated as being in the form of a plate with two distinct cam channels, differently configured approximation members are envisioned. For example, a single cam channel may be provided to engage two cam followers. Further, the cam channels need not be confined but rather can be formed on the surface of a plate, bar or the like. In such a device, the anvil may be urged by a biasing member to the closed or clamped position.

Although one or more actuators has not been disclosed to advance the approximation member and/or fire staples from the cartridge assembly, it is envisioned that one or more of a variety of known pivotable, rotatable, or slidable actuators, e.g., trigger, knob, lever, etc., may be used to approximate the presently disclosed cartridge assembly and/or fire staples from the cartridge. It is also noted that the disclosed tool assembly may be or form the distal portion of a disposable loading unit or may be incorporated directly into the distal end of a surgical instrument, e.g., surgical stapler, and may include a replaceable cartridge assembly.

FIGS. 5-10 disclose another preferred embodiment of the presently disclosed tool assembly shown generally as 100. Tool assembly 100 includes an anvil 112 and a cartridge assembly 114, an approximation member 116, and an elongated body portion 120 including an articulation joint generally referred to as 122. Elongated body portion 120 may form the proximal end of a disposable loading unit or the distal end of a surgical stapling device. Tool assembly 100 also includes a combined articulation and firing actuation mechanism 124 for articulating tool assembly 100 about articulation joint 122 and ejecting staples from cartridge assembly 114. Although the articulation joint illustrated as a flexible corrugated member with preformed bend areas, articulation joint 122 may include any known type of joint providing articulation, e.g., pivot pin, ball and socket joint, a universal joint etc.

Figure 7:
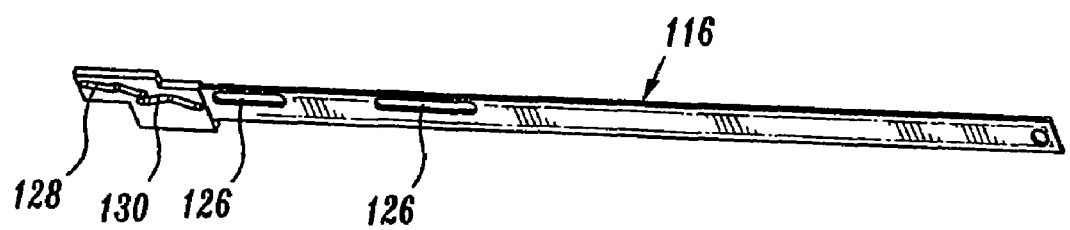
FIG. 7 is a side perspective view of the approximation member of the tool assembly shown in FIG. 6.
Figure 8:
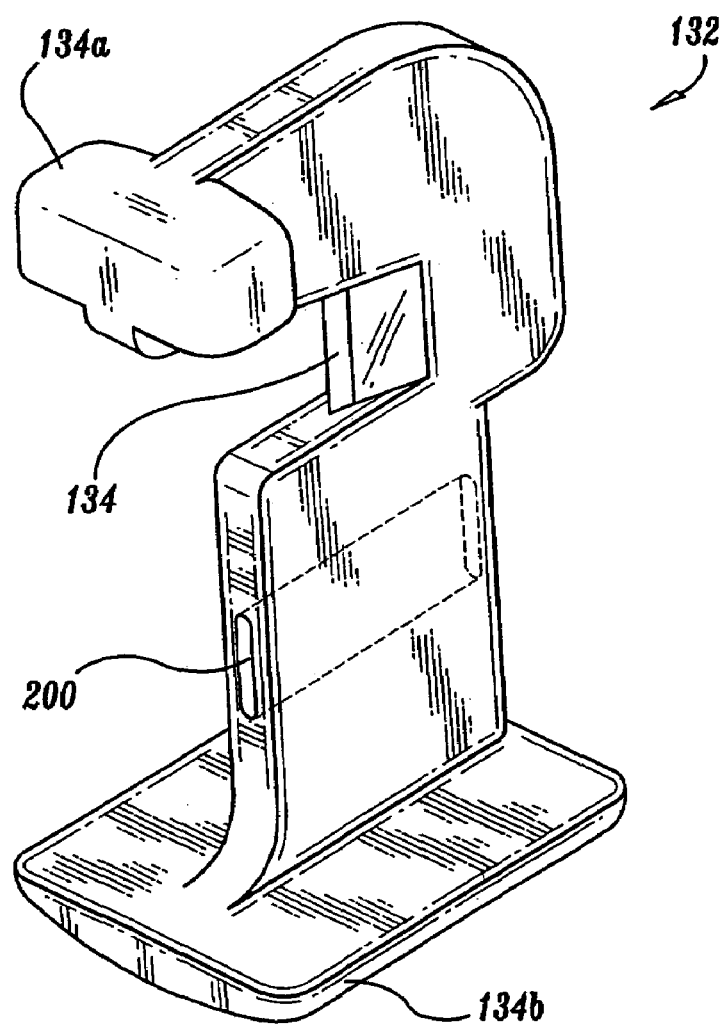
FIG. 8 is a side perspective view of the dynamic clamping member of the tool assembly shown in FIG. 6.

Approximation member 116 is substantially similar to approximation member 16 and also includes cam channels 128 and 130 (FIG. 7). Approximation member 116 further includes a pair of guide channels 126. Guide channels 126 are dimensioned to receive guide pins 128 which extend through elongated body portion 120 and function to maintain approximation member 116 along a linear path of travel. Approximation member 116 is constructed from a flexible material, e.g., spring steel, which is capable of bending around articulation joint 122. Alternately, it is envisioned that approximation member 116 may include a resilient rod, band or the like with cam surfaces formed thereon. Approximation member 116 operates in substantially the same manner as approximation member 16 and will not be discussed in further detail herein.

Cartridge assembly 114 includes a support channel 118, a sled 131 and a dynamic clamping member 132 which, preferably, includes an upper flange 134a for slidably engaging a bearing surface of the anvil and lower flange 134b for slidably engaging a bearing surface of the cartridge. A knife blade 134 is preferably supported on a central portion 134c of dynamic clamping member 132 to incise tissue. Knife blade may be secured to dynamic clamping member 132 in a removable or fixed fashion, formed integrally with, or ground directly into dynamic clamping member 132. Sled 131 is slidably positioned to translate through cartridge 114 in a known manner to eject staples from the cartridge. Sled 131 or the like can be integral or monolithic with dynamic clamping member 132. Sled 131 is positioned distal of and is engaged and pushed by dynamic clamping member 132. The position of 131 is to effect firing or ejection of the staples to fasten tissue prior to cutting the stapled tissue. Flange 134b preferably is positioned within a recess 138 formed in the base of cartridge 114. Flange 134a is preferably positioned within a single or separate recess formed in anvil 112. Again, flanges 134a and 134b need not be positioned in a recess but can slidably engage a respective surface of the anvil and cartridge. Dynamic clamping member 132 preferably is positioned proximal of sled 130 within cartridge assembly 114. Dynamic clamping member 132 functions to provide, restore and/or maintain the desired tissue gap in the area of tool assembly 100 adjacent sled 130 during firing of staples.

It is preferred that the anvil and preferably the dynamic clamping member be formed of a material and be of such a thickness to minimize deflection of the anvil and dynamic clamping member during firing of the device. Such materials include surgical grade stainless steel. The anvil is preferably formed as a solid unit. Alternatively, the anvil may be formed of an assembly of parts with conventional components.

Figure 9:
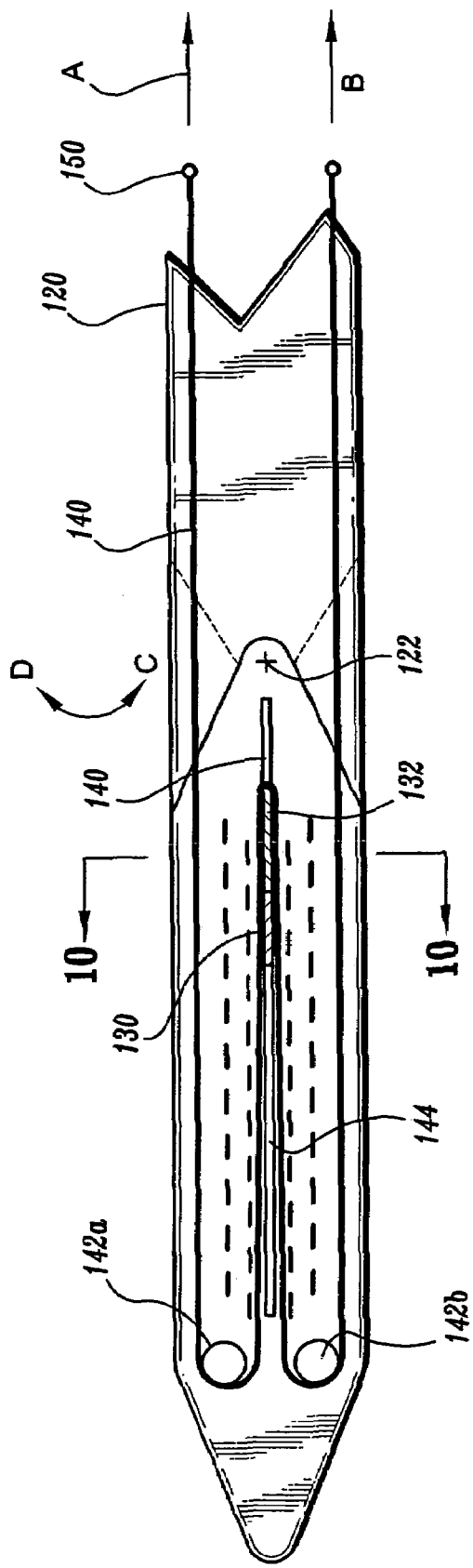
FIG. 9 is a top partial cross-sectional view with portions broken away looking through a portion of the cartridge assembly and showing the articulation and firing actuator of the tool assembly shown in FIG. 6.
Figure 10:
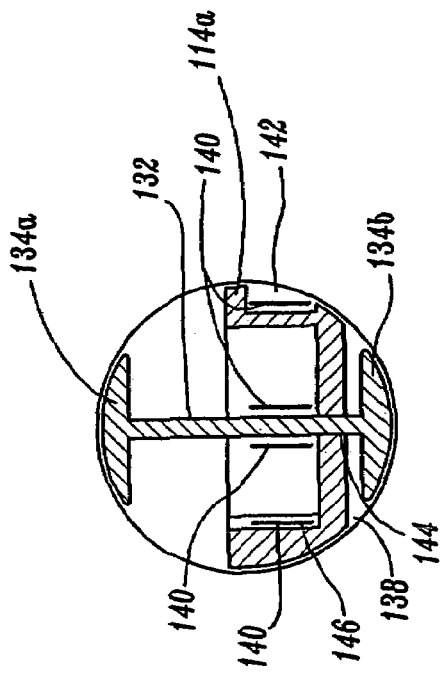
FIG. 10 is a cross-sectional view with portions removed and portions added, as would be seen along section lines 10-10 of FIG. 9.

Referring to FIGS. 6, 9 and 10, articulation and firing mechanism 124 includes a tension member 140 which can have loops 124 or other connection portions or connectors for connection to suitable connection members of one or more actuators or of an actuation mechanism. Although illustrated as a flexible band, tension member 140 may be or include one or more of any flexible drive member having the requisite strength requirements and being capable of performing the functions described below, e.g., a braided or woven strap or cable, a polymeric material, a para-aramid such as Kevlar™, etc. Kevlar™ is a trade designation of poly-phenyleneterephthalamide commercially available from DuPont. A pair of suitable fixed or rotatable members, preferably rollers 142a and 142b, are secured at the distal end of cartridge assembly 114. Rollers 142a and 142b may be formed or supported in a removable cap 114b (FIG. 6) of cartridge assembly 114. Alternately, cap 114b may be formed integrally with staple cartridge 114a or cartridge channel 118. Rollers 142a and 142b can also be secured to or formed from cartridge support channel 118. Tension member 140 extends distally from elongated body 120 of tool assembly 100, distally through a peripheral channel 142 in staple cartridge 114a, around roller 142a, proximally, preferably, alongside central longitudinal slot 144 formed in cartridge 114a, through a slot 200, preferably a transverse slot, in or around a proximal portion of dynamic clamping member 132, distally around roller 142b, and again proximally through a channel 146 formed in cartridge 114a to a proximal portion of elongated body 120. Alternately, two tension members can be employed, each of which may be secured to dynamic clamping member 132. As illustrated in FIG. 10, channels 142 and 146 can be at least partly defined by an inner and/or outer wall of cartridge 114a and/or by cartridge support channel 118. Unlike as shown, channels 142 and 146 should be in a consistent, i.e., same, functionally same or corresponding location on both sides of the staple cartridge. Thus, it is envisioned that there would be two peripheral channels 142, or two channels 146.

In use, when a first end or portion 150 of tension member 140 is retracted by suitable means in the direction indicated by arrow "A", as viewed in FIG. 9, tool assembly 100 will articulate about pivot member 122a in the direction indicated by arrow "D". When second end or portion 152 of tension member 140 is retracted in the direction indicated by arrow "B", tool assembly 100 will articulate in the direction indicated by arrow "C". When both ends of tension member 140 are retracted simultaneously, tension member 140 will advance dynamic clamping member 132 distally through slot 144 in cartridge 114a to advance dynamic clamping member 132 and sled 130 through cartridge 114a and by engaging pushers, eject staples from the cartridge and incise tissue in the tissue gap. In order to prevent dynamic clamping member 132 from advancing through slot 144 when the tool assembly is being articulated, i.e., when only one end of tension member 140 is retracted, a lockout device (not shown), e.g., a shear pin, may be provided to prevent movement of the dynamic clamping member or delay it until a predetermined force has been applied to the dynamic clamping member. It is envisioned that multiple tension members, e.g., bands, can be employed, respectively, to perform individual or a combination of functions. For example, a pair of tension members can be employed, one to articulate, and the other to approximate, clamp and fire. The tension members can be fixed to the dynamic clamping member or a knife carrying member or to a combination dynamic clamping member, knife member and/or sled member.

The above-described tool assembly may be incorporated into a disposable loading unit such as disclosed in U.S. Pat. No. 6,330,965 or attached directly to the distal end of any known surgical stapling device. Although a handle assembly for actuating the approximation member and the combined articulation and firing mechanism have not been specifically disclosed herein, it is to be understood that the use of a broad variety of different actuating mechanisms and handle configurations are envisioned including toggles, rotatable and slidable knobs, pivotable levers or triggers, pistol grips, in-line handles, remotely operated systems and any combination thereof. The use of an above-described tool assembly as part of a robotic system is envisioned.

It will be understood that various modifications may be made to the embodiments disclosed herein. For example, although this application focuses primarily on the use of surgical staples, other fastening devices, such as two-part fasteners, may be included in this device. In a device in which two-part fasteners are used, each of the anvil staple forming pockets may be configured to receive one part of the two-part fastener. Further, it is envisioned that the teachings provided in this disclosure may be incorporated into surgical devices other than stapling devices including graspers. Therefore, the above description should not be construed as limiting, but merely as exemplifications of preferred embodiments. Those skilled in the art will envision other modifications within the scope and spirit of the claims appended hereto.

What is claimed is:

1. A tool assembly comprising:
   a pair of jaws including a first jaw and a second jaw, each of the jaws having a proximal end and a distal end, the first and second jaws being movable in relation to the other;
   first and second cam followers supported on the first jaw; and
   an approximation member including at least one cam surface positioned to engage the first and second cam followers, the approximation member being movable through an actuating stroke to move the at least one cam surface in relation to the first and second cam followers;
   wherein the approximation member is movable to move the at least one cam surface in relation to the first and second cam followers to effect movement of the first jaw to approximate a distal end of the first jaw with the second jaw in a first portion of the actuating stroke, to subsequently move the distal end of the first jaw away from the second jaw in a second portion of the actuating stroke, and to subsequently bring together the first jaw and the second jaw in substantially parallel closure in a third portion of the actuating stroke.

2. A tool assembly according to claim 1, wherein the first jaw includes an anvil and the second jaw includes a cartridge assembly, the cartridge assembly housing a plurality of staples.

3. A tool assembly according to claim 1, wherein the at least one cam surface includes at least one cam channel.

4. A tool assembly according to claim 3, wherein the at least one cam channel includes first and second cam channels.

5. A tool assembly according to claim 1, wherein the approximation member includes a flat plate having the at least one cam surface formed therein.

6. A tool assembly according to claim 5, wherein the first jaw includes a longitudinal slot formed in its proximal end, the approximation member being slidably positioned in the longitudinal slot.

7. A tool assembly according to claim 6, wherein the first and second cam followers are supported on the proximal end of the first jaw and extend across the longitudinal slot adjacent the at least one cam surface.

8. A tool assembly according to claim 7, wherein the at least one cam surface includes first and second cam channels, the first cam follower extending through the first cam channel and the second cam follower extending through the second cam channel.

9. A tool assembly according to claim 1, further including a body portion, wherein the tool assembly is pivotally attached to the body portion by an articulation joint.

10. A tool assembly according to claim 9, wherein the body portion forms a distal end of a surgical stapling device.

11. A tool assembly according to claim 1, wherein the body portion forms the proximal portion of a disposable loading unit.

12. A tool assembly according to claim 1, wherein the first jaw is an anvil and the second jaw is a cartridge assembly housing including a plurality of staples.

13. A tool assembly according to claim 12, further comprising:
   a body portion, wherein the tool assembly is pivotally attached to the body portion by an articulation joint;
   a dynamic clamping member being movable in relation to the anvil and the cartridge assembly to eject the staples from the cartridge assembly; and
   an articulation and firing actuator extending at least partially through the body portion and the tool assembly, the articulation and firing actuator being operably associated with the dynamic clamping member and the tool assembly and being movable in relation thereto to selectively pivot the tool assembly in relation to the body portion and move the dynamic clamping member in relation to the tool assembly to effect ejection of the staples from the cartridge.

14. A tool assembly according to claim 13, wherein the articulation and firing actuator includes a flexible band having a first end portion extending at least partially through the body portion and through the cartridge assembly, a central portion extending from the first end portion and being operatively associated with the dynamic clamping member and a second end portion extending from the central portion through the cartridge assembly and at least partially through the body portion to a position adjacent the first end.

15. A tool assembly according to claim 14, wherein actuation of the first end portion articulates the tool assembly in one direction and actuation of the second end portion articulates the tool assembly in an opposite direction.

* * * * *